United States Patent [19]

Jones

[11] Patent Number: 5,116,607
[45] Date of Patent: May 26, 1992

[54] HAIR DRESSING

[76] Inventor: Alma L. Jones, 19232 S. Cliveden, Carson, Calif. 90746

[21] Appl. No.: 485,943

[22] Filed: Feb. 27, 1990

[51] Int. Cl.$^5$ ................................................. A61K 7/11
[52] U.S. Cl. ........................................ 424/70; 424/71; 424/74; 424/195.1
[58] Field of Search ........................ 424/70, 74, 195.1; 514/783

[56] References Cited

U.S. PATENT DOCUMENTS 3,932,611  1/1976  McCarthur ............................ 424/70
3,980,768  9/1976  White ..................................... 424/70
4,180,561  12/1979  Vinson ................................... 424/70

FOREIGN PATENT DOCUMENTS 2303529  11/1976  France ................................... 424/70
52-38011  3/1977  Japan ..................................... 424/70
2124903  2/1984  United Kingdom .................. 424/70

Primary Examiner—Thurman K. Page
Attorney, Agent, or Firm—Ladas & Parry

[57] ABSTRACT

Disclosed herein is a hair dressing comprised of petrolatum, carbowax 940, PEG-75 lanolin, caster oil, amber wax, paraffin wax, biotin, keratin, placenta, and polysorbate 80.

11 Claims, No Drawings

HAIR DRESSING

BACKGROUND OF THE INVENTION

On the market today are a wide variety of creams, oils, lotions and the like for treating the scalp or the hair of an individual. The present invention discloses a compound for treating both the hair and scalp to enhance the look of the hair as well as to moisturize the hair and scalp. The cream results in a more lustrous, fuller look to the head of hair and a softer, more pliable feel to the scalp.

SUMMARY OF THE INVENTION

The present invention is a hair dressing comprised of: petrolatum (light); CARBOWAX 940 (a trade name for Polyethylene Glycol (PEG); PEG-75 (a trade name for the product Solulan L-575 a water soluble lanolin that is 50% aqueous) lanolin; castor oil; AMBERWAX (a trade name for microcrystalline wax); paraffin wax; biotin; keratin; placenta; and polysorbate 80 an oleate ester of sorbitol and its anhydrides copolymerized with approximately 20 moles of ethylene oxide for each mole of sorbitol an sorbitol anhydrides).

DESCRIPTION OF THE INVENTION

The following is a preferred embodiment of the method of making the present invention. This method involves essentially three Phases. In the first Phase, Phase I, petrolatum (light) is heated to approximately 80° centigrade until it is melted. For the following measurements, preferably 9,280 grams of petrolatum (light) are used. To the heated petrolatum (light) is then added 1,160 grams of CARBOWAX 940 (a trade name for polyethylene glycol (PEG) and 1,160 grams of stearic acid. These items should be added to the petrolatum (light) while keeping the temperature of the petrolatum (light) and other ingredients at about 80 degrees centigrade and while stirring the mixture constantly. Next added are 1,160 grams of cetyl alcohol, 1,160 grams of glycerol stearate, and 2,320 grams of light mineral oil. Each item added to the already mixed items should be allowed to melt if necessary, before adding the following item and the mixture at all times should be stirred and the temperature kept very close to 80 degrees centigrade.

When all items have been added, the combination of the foregoing should be stirred moderately until fully mixed and then cooled to approximately 75 degrees centigrade. Upon reaching the 75 degree centigrade temperature, the following items should be added while mixing and maintaining the mixture at about 75 degrees centigrade: 200 grams of PEG-75 lanolin, 232 grams of olive oil, 232 grams of castor oil, 464 grams of isopropyl myristate, 232 grams of Jo Jo oil (jojoba oil), 232 grams of squalene, 1 gram of mineral wax, 1 gram of wheat germ oil, 116 grams of coconut oil, 50 grams of sesame oil, 1 gram of mink oil, and 5 grams of vitamin E.

In Phase II, AMBERWAX (a trade name for micro crystalline wax) and paraffin wax are melted together in a separate container. This Phase II mixture should be made concomitant with the start of the preparation of Phase I. Specifically, 348 grams of AMBERWAX (a trade name for microcrystalline wax) and 232 grams of paraffin wax should be melted together and heated until the two waxes reach a temperature of 85° centigrade This mixture should then be stirred into the Phase I mixture preferably after the addition of the mineral wax.

The above-noted Phase I and Phase II items should be stirred together until fully mixed and liquid. With the stirring continuing, the temperature of the mixture should be allowed to drop to about 65 degrees centigrade at which time the following Phase III items should be added while stirring: 1 gram of quinine, 1 gram of biotin, 1 gram of paba, 1 gram of keratin protein, 1 gram of DNA, 464 grams of lecithin, 232 grams of polysorbate 80, 464 grams of almond oil, 5 grams of vitamin A & D oil, and 200 grams of fragrance. During the addition of the foregoing items the 65 degree centigrade temperature should be maintained.

After mixing together all of the foregoing items, the complete combination of ingredients should be thoroughly stirred, making sure the temperature remains at about 65° centigrade and then left to cool. The result is a hair and scalp treatment which is pleasant in use and seems to lead to a healthier scalp and apparently a thicker head of hair.

Of the foregoing ingredients, those that are most important are the petrolatum CARBOWAX 940 (a trade name for Polyethlylene Glycol (PEG) (light), PEG-75 lanolin, (2 trade name for the product Solulan L-575 a water soluble lanolin that is 50% aqueous, castor oil, AMBERWAX (a trade name for microcrystalline wax) paraffin wax, biotin, keratin protein, and polysorbate 80. Placenta may also be included and may be included as a keratin protein containing placenta. In fact, with such inclusion, the keratin protein without placenta could then be replaced by the keratin protein with placenta or placenta. The remaining ingredients are added for cosmetic purposes only.

In lieu of or as another name for certain of the foregoing ingredients it is noted that steralkonium chloride may be used instead of PEG-75 lanolin (a trade name for the product solulan L-575 a water soluble lanolin that is 50% aqueous and isopropyl myristate; hydrolyzed protein may replace the Keratin Protein; TWEEN 80 is the trade name for Polysorbate 80; and certyleth may replace the cetyl alcohol. The gram amount of these replacements will be the same as the gram amount of the item replaced.

It is advisable to continue mixing the mixture from start to finish to ensure the thorough combination of all ingredients.

Optional ingredients which may be added during any Phase but preferably in Phase III are sulfur, aloe vera and coconut oil.

The present invention is claimed as follows.

1. A hair dressing comprised of: petrolatum (light); CARBOWAX 940 (a trade name for the product polyethylene glycol (PEG); PEG-75 lanolin (a trade name for the product Solulan L-575 a water soluble lanolin that is 50% aqueous); castor oil; AMBERWAX (a trade name for micro crystalline wax): paraffin wax; biotin; keratin protein; and polysorbate 80.

2. A method of manufacturing a hair dressing comprised of:
   a) heating petrolatum (light) to 80 degrees centigrade;
   b) adding to said petrolatum (light) while mixing and maintaining the above temperature, melted CARBOWAX 940 (a trade name for polyethylene glycol (PEG);
   c) allowing the mixture of petrolatum (light) and CARBOWAX 940 to cool to 75 degrees centigrade and then maintaining the 75 degree centigrade temperature of the mixture while mixing therein PEG 75 lanolin (a trade name for the product Solulan L-575 a water soluble lanolin that is 50% aqueous); castor oil; and melted AMBERWAX (a trade name for microcrystalline wax) mixed with melted paraffin wax;

d) continuing to stir the mixture while allowing it to cool to 65 degrees centigrade; and e) adding to the foregoing mixture when at the 65 degree centigrade level biotin, keratin protein containing placenta, and polysorbate 80, said biotin, keratin protein containing placenta and polysorbate 80 being added while mixing the mixture and maintaining the mixture at 65 degrees centigrade.

3. The hair dressing of claim 1 wherein 9280 grams of petrolatum light are to be used to 1160 grams of CARBOWAX 940; 200 grams of PEG-75 lanolin; 232 grams of castor oil; 348 grams of AMBERWAX; 232 grams of paraffin wax; 1 gram of biotin; 1 gram of keratin protein; 232 grams of polysorbate 80.

4. The hair dressing of claim 2 wherein 9280 grams of petrolatum light are to be used to 1160 grams of CARBOWAX 940; 200 grams of PEG-75 lanolin; 232 grams of castor oil; 348 grams of AMBERWAX; 232 grams of paraffin wax; 1 gram of biotin; 1 gram of keratin protein; 232 grams of polysorbate 80.

5. A hair dressing comprised of: 9280 grams of petrolatum (light); 1160 grams each of CARBOWAX 940 (a trade name for polyethylene glycol (PEG); stearic acid; cetyl alcohol; and glycerol stearate; 2320 grams of light mineral oil; 200 grams of PEG-75 lanolin (a trade name for Solulan L-575 a water soluble lanolin that is 50% aqueous); 232 grams each of olive oil, castor oil, jojoba oil, and squalene; 464 grams of isopropyl myristate; 1 gram each of mineral wax, wheat germ oil and mink oil, 116 grams of coconut oil; 50 grams of sesame oil; 5 grams of vitamin E; 348 grams of AMBERWAX (a trade name for microcrystalline wax); 232 grams of paraffin wax; 1 gram each of quinine; biotin; paba; keratin protein; DNA; 464 grams of lecithin; 232 grams of polysorbate 80; 464 grams of almond oil; 5 grams of vitamins A and D oil; and 200 grams of fragrance.

6. The hair dressing of claim 5 further comprising at least one of sulfur, aloe vera, and coconut oil.

7. The method of manufacturing the hair dressing of claim 5 comprising the steps of:

heating the petrolatum (light) until it is melted;

adding the CARBOWAX 940 and the stearic acid to the petrolatum (light) while stirring constantly;

adding when in a liquid state, the cetyl alcohol, glycerol stearate and light mineral oil to the foregoing mixture;

cooling the mixture of all of the above materials and thereafter adding the PEG-75 lanolin; olive oil; castor oil; isopropyl myristate; jojoba oil; squalene; mineral wax; wheat germ oil; coconut oil; sesame oil; mink oil; and vitamin E;

melting together in a separate container the AMBERWAX and paraffin wax and adding these two ingredients to the above mixture of ingredients; and adding to the foregoing mixture while stirring, the quinine, biotin, paba, kertin protein, DNA, lecithin, polysorbate 80, almond oil, vitamins A and E and fragrance.

8. The method of claim 7 further comprising the step of adding at least one of sulfur, aloe vera oil, or coconut oil.

9. The method of claim 7 wherein the ingredients should be stirred at all times and a temperature kept such that all ingredients are in a liquid state when being mixed with each other.

10. A method of manufacturing a hair dressing comprised of:

a) heating petrolatum (light) until it is melted;

b) adding to said petrolatum (light) while mixing, melted CARBOWAX 940 (a trade name for polyethylene glycol (PEG));

c) allowing the mixture of petrolatum (light) and CARBOWAX 940 to cool and then mixing therein PEG 75 lanolin (a trade name for the product Solulan L-575 a water soluble lanolin that is 50% aqueous); castor oil; and melted AMBERWAX (a trade name for micro crystalline wax) mixed with melted paraffin wax;

d) continuing to stir the mixture while allowing it to cool, and e) adding to the foregoing mixture biotin, keratin protein containing placenta, and polysorbate 80, said biotin, keratin protein containing placenta and polysorbate 80 being added while mixing the mixture.

11. The method of claim 10 wherein the ingredients should be stirred at all times and a temperature kept such that all ingredients are in a liquid state when being mixed with each other.

* * * * *